US010653563B2

(12) United States Patent
Lilien (10) Patent No.: US 10,653,563 B2
(45) Date of Patent: May 19, 2020

(54) BRA LINERS (71) Applicant: Donna Lilien, Kiryat Motzkin (IL)

(72) Inventor: Donna Lilien, Kiryat Motzkin (IL)

( * ) Notice: Subject to any disclaimer, the term of this patent is extended or adjusted under 35 U.S.C. 154(b) by 922 days.

(21) Appl. No.: 14/802,047

(22) Filed: Jul. 17, 2015

(65) Prior Publication Data

US 2017/0013887 A1 Jan. 19, 2017

(51) Int. Cl.
*A61F 13/14* (2006.01)
*A41C 3/14* (2006.01)

(52) U.S. Cl.
CPC .............. *A61F 13/145* (2013.01); *A41C 3/14* (2013.01); *A41C 3/144* (2013.01)

(58) Field of Classification Search
CPC ............ A61F 13/14; A61F 2013/15016; A61F 13/15; A61F 13/145; A41D 27/12; A41C 3/12; A41C 3/06; A41C 3/065; A41C 3/144; A41C 3/14; A41C 3/0078; A41B 2300/24
USPC ............................... 604/358; 450/93, 37, 81
See application file for complete search history.

(56) References Cited

U.S. PATENT DOCUMENTS

| | | | |
|---|---|---|---|
| 3,446,213 A | 5/1969 | Goldman | |
| 5,603,653 A | 2/1997 | Hartman | |
| 5,664,984 A | 9/1997 | Laughridge | |
| 5,690,536 A | 11/1997 | Madden et al. | |
| 5,858,014 A | 1/1999 | Kepes et al. | |
| 5,980,359 A | 11/1999 | Brown | |
| 6,203,399 B1 | 3/2001 | Hackney | |
| 6,264,530 B1 | 7/2001 | Cosentino | |
| 6,341,377 B1 * | 1/2002 | Faries, Jr. .............. | A41D 27/13 2/53 |
| 6,464,717 B1 | 10/2002 | Smith et al. | |
| 7,335,086 B1 * | 2/2008 | Karon .................... | A41C 3/065 450/1 |
| 7,793,358 B2 | 9/2010 | Frye | |
| 7,794,304 B2 | 9/2010 | Frye | |
| 7,905,763 B1 * | 3/2011 | Frank .................... | A61F 13/141 450/37 |

(Continued)

FOREIGN PATENT DOCUMENTS

DE 10202410 A 8/2003

OTHER PUBLICATIONS

International Search Report and Written Opinion for PCT/IL2016/050748 dated Nov. 29, 2016.

(Continued)

*Primary Examiner* — Alissa J Tompkins
*Assistant Examiner* — Brieanna Szafran
(74) *Attorney, Agent, or Firm* — Brian Roffe (57) ABSTRACT

Bra liner including a substantially planar body including a left triangular portion, a right triangular portion and a central portion between the left and right triangular portions. The central portion includes a flap separated from the left and right triangular portions and optionally one or more apertures. The left and right triangular portions also optionally include one or more apertures. The flap is foldable about a center line of the body. The body includes absorbent material. To form the left and right triangular portions, an elongate slit is present between the central portion and each of the left and right triangular portions. The slits extend downward from an upper edge of the body and inward toward the center line.

16 Claims, 8 Drawing Sheets

(56) References Cited

U.S. PATENT DOCUMENTS

| | | |
|---|---|---|
| 8,246,416 B2 | 8/2012 | Frye |
| 2010/0101586 A1 | 4/2010 | Frye |
| 2010/0105286 A1* | 4/2010 | Frye .................... A61F 13/145 |
| | | 450/57 |
| 2012/0157951 A1 | 6/2012 | Johnson |
| 2014/0302745 A1* | 10/2014 | Golubovic ............ A61F 13/15 |
| | | 450/1 |
| 2015/0150310 A1* | 6/2015 | Perl ........................ A41C 3/12 |
| | | 450/93 |
| 2017/0172218 A1* | 6/2017 | Khan ..................... A61L 15/40 |

OTHER PUBLICATIONS

QVCTV Girlease set of 12 disposable bra liners with Nancy Hornbeck, Youtube, Jun. 17, 2015, retrieved Oct. 28, 2016.
Bra Liner (Undated).

* cited by examiner

BRA LINERS

FIELD OF THE INVENTION

The present invention relates generally to an article of clothing for use as a bra liner and more particularly, to a hygienic product for absorbing perspiration from the breasts.

The present invention also relates to methods for absorbing moisture around breasts of a person using an article of clothing.

BACKGROUND OF THE INVENTION

Brassieres, commonly known as bras, are undergarments made to support a woman's breasts. The cup of the bra is designed to contain the breast. Bra wearers complain of perspiration in the under-bra area. Consequently, there is a need for a product that keeps the wearer dry and comfortable.

U.S. Pat. No. 8,246,416 (Frye) describes a foldable one-piece insert worn between the bra and the body having irritation reducing and/or absorbent material portions which line the bra cup and that lie under the supported breast, and portions which extends toward the torso rear under the bra side straps and a portion extending below the bra line along the torso.

U.S. Pat. No. 6,464,717 (Smith et al.) describes a bra with hot/cold inserts for a therapeutic device in the form of a vest-like elastic garment adapted to be worn on the human upper torso. The device includes front panels having pockets therein for retaining gel packs.

U.S. Pat. No. 5,690,536 (Madden et al.) describes a disposable bra liner comprising three cup-shaped coextensive layers attached together, with each layer presenting a circular periphery. The bra liners further include a structural member attached to the layers for maintaining the shape of the pad. The structural member includes an elastic band attached to the layers at their peripheries and preferably has a plurality of V-shaped folding portions. The invention is held in place with the V shaped flaps (which therefore must be folded over), which does not offer the option of folding or unfolding the V-shaped folding portions, pursuant to the wearer's choice.

U.S. Pat. No. 5,664,984 (Laughridge) describes a bra having a torso encircling body portion having a frontal portion, a pair of side portions and a back portion. A pair of breast cups is located in the frontal portion on either side of an area connecting the breast cups. Moisture absorbent material is attached to the area between the breast cups. The moisture absorbent material is thin and preferably shaped to fit the contour of the brassiere between the breast cups. It may be attached to the inside of the bra using a conventional adhesive such as those used with panty liners and the like.

U.S. Pat. Appln. Publ. No. 20120157951 (Johnson) describes a bra liner which has a first sheet of fluid-pervious non-woven material having a first edge and a second edge. A second sheet of fluid pervious non-woven material having a first edge and a second edge is positioned in adjacent relationship to the first sheet. The first edge of the second sheet is joined to the first edge of the first sheet and the second edge of the second sheet is joined to the second edge of the first sheet. A breathable compartment is formed between the first and second sheets. A layer of superabsorbent gel material and cotton fluff is positioned in the compartment.

U.S. Pat. Appln. Publ. No. 20150150310 (Perl) describes a lining to be placed between the inner lining of a bra and the skin of the breasts. The lining includes an outer protective non-woven material layer that attaches to the bra from the inside with an adhesive, a middle absorbent layer adapted to absorb bodily fluids, a comfortable material-based inner layer that comes in contact with the skin, and two lower flaps protruding from the bottom of the lining and out of the bra. The flaps include flexible material adapted to be folded outward to connect to the outer portion of the bra.

DE 102 02 410 (Mueller) describes an absorption element (2) that has a half moon or V shape when viewed from above and is placed into a bra, which holds it in the sub-mammary breast (3) area. The element contains deodorants or antiperspirants.

SUMMARY OF THE INVENTION

A basic embodiment of a bra liner in accordance with the invention includes a substantially planar body including a left portion, a right portion and a central portion between the left and right portions. The central portion includes a flap separated from the left and right portions. In most embodiments, the flap is foldable about a center line of the body. The body includes one or more absorbent materials. In some embodiments, the flap includes an aperture (or cut-out) and in others, an additional aperture is situated in the central portion below the aperture in the flap. Also, the right and left portions may each include one or more apertures. In other embodiments, the aperture in the flap opens to a top edge of the body to thereby form an indentation.

In most embodiments, the left and right portions each have a generally triangular foldable part and a non-foldable part. A first elongate slit is between the central portion and the triangular foldable part of the left portion and a second elongate slit is between the center portion and the triangular foldable part of the right portion. The slits extend downward from an upper edge of the body and inward toward the center line. The left and right portions are foldable about a fold line passing through inward ends of the slits.

In some embodiments, the flap includes at least one stitch line enabling removal of a portion of the flap by tearing of the flap along each stitch line.

An adhesive portion may be provided at a tip region of each of the right and left portions. A respective cover strip covers each of the adhesive portions and the cover strips are removable to enable adhesive attachment of the body to a bra.

The body may have a truncated triangular shape having a bottom that is common to the right, left and central portions, an angled left side of the left portion forming a left side of the truncated triangular shape of the body and an angled right side of the right portion forming a left side of the truncated triangular shape of the body.

An article of clothing in accordance with the invention includes a body having a truncated triangular shape and material adapted to absorb body perspiration. The body includes a first elongate slit extending downward and inward toward a center line of the body from a left side of the body to thereby define a left triangular portion above a fold line of the body, and a second elongate slit extending downward and inward toward a center line of the body from a right side of the body to thereby define a right triangular portion above the fold line of the body. The body also includes a central portion between the left and right triangular portions. The central portion defines at least one aperture, possibly in a flap over the fold line. Inner ends of the first and second slits are on the fold line, which, when being pushed inwardly, facilitates folding of the left and right triangular portions forward.

The left triangular portion may be part of a left wing and the right triangular portion may be part of a right wing. The central portion is connected to the right and left wings. The right wing has a non-foldable part below the fold line and the left wing has a non-foldable part below the fold line. An adhesive portion may be provided at a tip region of each of the left and right triangular left portions and a respective cover strip covers the adhesive portion. The cover strips are removable to enable adhesive attachment of the body to a bra.

The invention also includes a method of absorbing moisture around breasts of a person. In this method, a bra liner is inserted between the skin of the chest and skin of each of the breasts, and partly between the breasts. The bra liner includes a substantially planar body including a left portion, a right portion and a central portion between the left and right portions. The central portion includes a flap partly separated from the left and right portions. The right portion is placed alongside a right breast and the left portion is placed alongside a left breast such that the central portion is between the right and left breasts. The flap is optionally about a center line of the body to thereby interpose the folded flap between the right and left breasts and maintain the right and left breasts out of contact with one another. The body includes absorbent material.

Optionally, the bra liner includes an adhesive portion at a tip region of each of the right and left portions, and a respective cover strip covering the adhesive portion. In this case, the cover strips are removed during insertion of the bra liner to expose the adhesive portions, and the exposed adhesive portions may be pressed against right and left portions of the bra.

The left and right portions may each have a generally triangular foldable part and a non-foldable part. In this case, inserting the bra liner entails folding the left and right triangular portions of the left and right portions outward such that a tip area of each of the left and right triangular portions overlies the non-foldable part of the respective left and right portions or extends to a location below the respective left and right portions.

BRIEF DESCRIPTION OF THE DRAWINGS

The invention, together with further objects and advantages thereof, may best be understood by reference to the following description taken in conjunction with the accompanying drawings, wherein like reference numerals identify like elements, and wherein.

DETAILED DESCRIPTION OF THE INVENTION

Referring to the accompanying drawings wherein like reference refer to the same or similar elements, several embodiments of a bra liner in accordance with the invention are shown in FIGS. 1A-1C, 2 and 3A-3C. There are common features of all of these bra liners. Unless indicated to the contrary, the features of one bra liner may be present in the other embodiments, to the extent possible. For example, all of the bra liners may be placed in a bra in accordance with the stages depicted in FIGS. 4A-4G with only minor variations, if any.

Figures 1A, 1D:
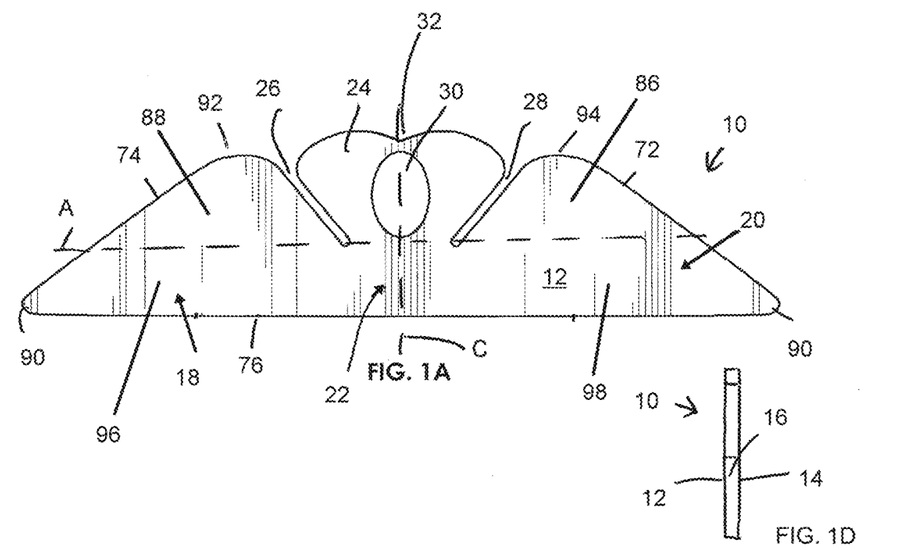
FIG. 1A is a schematic illustration of a first embodiment of a bra liner in accordance with the present invention.
FIG. 1D is a side view of the bra liner of any of FIGS. 1A, 1B and 1C.

The first embodiment of a bra liner in accordance with the invention is shown in FIG. 1A and designated 10. Bra liner 10 preferably has a substantially planar form, i.e., has an outer facing surface (first side) 12 and an inner facing surface (second side) 14 and a substantially uniform body 16 between the outer and inner facing surfaces 12, 14 (see FIG. 1D). Thus, the thickness of the body 16, between surfaces 12, 14, may be uniform and constant. The body 16 is preferably a three-part absorbent flat sheet defining the first and second sides, and sheet having up, down, right, and left directions in the plane of the sheet. Thus, in the orientation shown in FIG. 1A, the body 16 defines a left wing 18, a right wing 20, and a central portion 22 disposed between the left and right wings 18, 20 and shaped to define a flap 24 in the central portion 22.

To define the flap 24, elongate slits 26, 28 are formed in the body 16 oriented in a direction the right and left sides toward a centerline C of the body 16. The edges defining the slits 26, 28 are generally straight and parallel to one another and angled such that the inward end of each slit 26, 28 is closer to the center line C than the outward end of the slits 26, 28, which may be flared as shown. The top edge of the flap 24 may have an overall arcuate form from the slits 26, 28 to the centerline to thereby form a dip 32 at the centerline C. The flap 24 also includes a vertically oriented, oval aperture or cut-out 30 alongside the slits 26, 28, i.e., the bottom of the aperture 30 is a level which is the same as or above the lowest level of the slits 26, 28. One purpose of the cut-out 30 is to allow for air flow through the flap 24 and preventing anaerobic condition. By reciting that element 30 is an "oval aperture", shown in FIGS. 1A, 1B, 3A, 3B, 4B, 4C and 4D, it is inherent that the aperture 30 in these embodiments is a hole surrounded by material.

Another purpose is to reduce the weight of the flap 24 to enable it to be folded about a fold line C defined as a line passing through the center of flap 24 and aperture/cut-out 30. The fold line C aids in the use of the bra liner 10, as discussed below with reference to FIGS. 4A-4G.

Relative to the centerline C, the body 16 may be symmetric. As such, the slits 26, 28 are mirror images of one another, while the left and right wings 18, 20 are also of the same size and shape. By virtue of the presence of the slits 26, 28, the central portion 22 is thus effectively separated from the left wing 18 by the left slit 26 and from the right wing 20 by the right slit 28.

The body 16 may be considered to have a truncated triangular form with left and right corners. The bottom of the triangle is formed by the bottom border 76 of the body 16 extending between the left and right corners (which include tip regions 90, discussed below), the left side by the top edge of the left wing 18 (also referred to as the left peripheral border 74) and the right side by the top edge of the right wing 20(also referred to as the right peripheral border 72). The truncated portion results in the top edge of the flap 24 being the top edge of the truncated triangle. Also, the slit 26 results in the formation of a smaller triangular portion on the left side while the slit 28 results in the formation of a similarly sized smaller triangular portion on the right side. In other words, the left wing 18 may itself have a generally triangular shape while the right wing 20 also has a generally triangular shape.

A folding line A separates an upper generally triangular foldable part 88 and 86 and a lower non-foldable part 96 and 98 on each of the left and right wings 18, 20 (see FIG. 1A). For each of these generally triangular left and right wings 18, 20, the base is at a bottom of the body 16 and the sides (provided by an edge of the slits 26, 28) are angled upward to a point.

The area between the slits 26, 28 forms the central portion 22. The bottom border 76 is preferably straight along most of its length, while the right and left peripheral borders 72, 74 are also preferably straight from the extreme ends to the slits 26, 28. Curved portions 90 (formed at tip regions, one in each corner of the body 16) may be provided to directly connect the bottom border 76 to the right and left peripheral borders 72, 74 and curved portions 92, 94 provided to connect the right and left peripheral borders 72, 74 to the edges of the slits 26, 28 (as shown in, e.g., FIGS. 1A, 1B, 1C and 2).

Figure 1B:
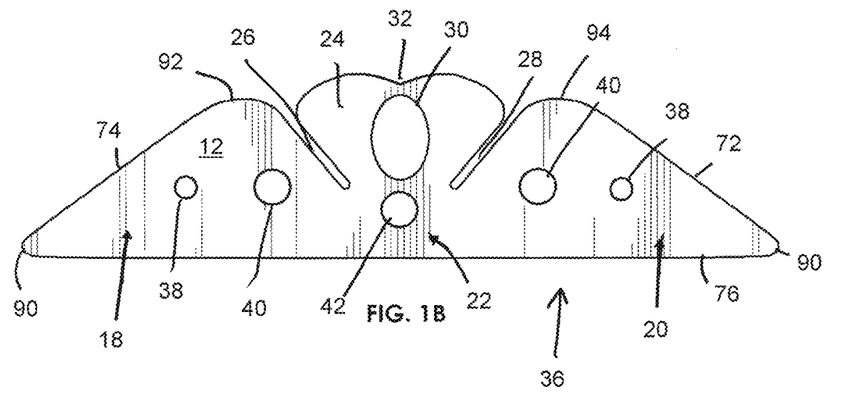
FIG. 1B is a schematic illustration of a second embodiment of a bra liner in accordance with the present invention.

The bra liner 36 in FIG. 1B differs from the bra liner 10 in that it shows additional apertures or cut-outs 38, 40, 42. Cut-outs 38 are closest to the left and right edges of the bra liner 36 and have a smaller size than cut-outs 40, 42. Cut-outs 40 are next inward of cut-outs 38, yet still in the left and right wings 18, 20. Cut-out 42 is on the central portion 22 below the cut-out 30 and may possibly be symmetrical about the centerline C. Cut-outs 38, 40, 42 may have a circular form as shown which means that they are circular holes surrounded by material. Cut-outs, as used herein, may be formed from the intentional removal of material forming the body 16. Alternatively, the body 16 may be formed with spaces where cut-outs would appear, and thus may be referred to generally as apertures.

Figure 1C:
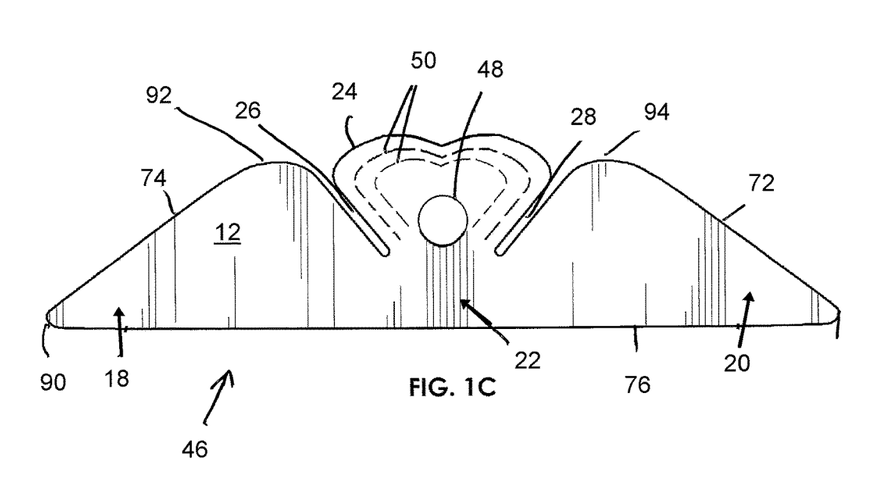
FIG. 1C is a schematic illustration of a third embodiment of a bra liner in accordance with the present invention.

The bra liner 46 in FIG. 1C is similar to that shown in FIG. 1A with the exception that the cut-out 48 in the flap 24 is circular. Generally, the shape of the cut-outs may vary and is not limited to any particular shape as shown or described herein. Moreover, different shaped cut-outs may be used in the various embodiments herein, e.g., an oval cut-out in the embodiment of FIG. 1C or a circular cut-out in the embodiment of FIG. 1A.

Also, the body 16 includes, in the central portion 22, one or more stitch lines 50 which allows each person to reduce the size of the bra liner 46 individually without the absorbent material disintegrating. The stitch lines 50 may generally form to the outer shape of the flap 24. More specifically, the user is able to reduce the size of the flap 24 by tearing along one of the stitch lines 50 until the bra liner 46 has a size appropriate for them. Obviously, the outermost stitch line 50 should be removed first and then proceed inward until the desired size is attained. The stitch lines 50 may be provided in any of the embodiments herein.

Figure 2:
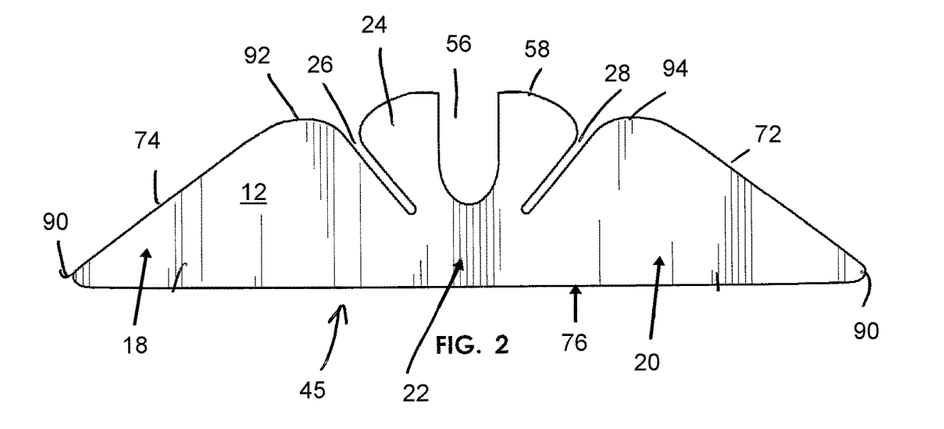
FIG. 2 is a schematic illustration of a fourth embodiment of a bra liner in accordance with the present invention.

The bra liner 54 in FIG. 2 shows an indentation 56 in the flap 24. The indentation 56 opens to a top edge 58 of the body 16.

Figure 3A:
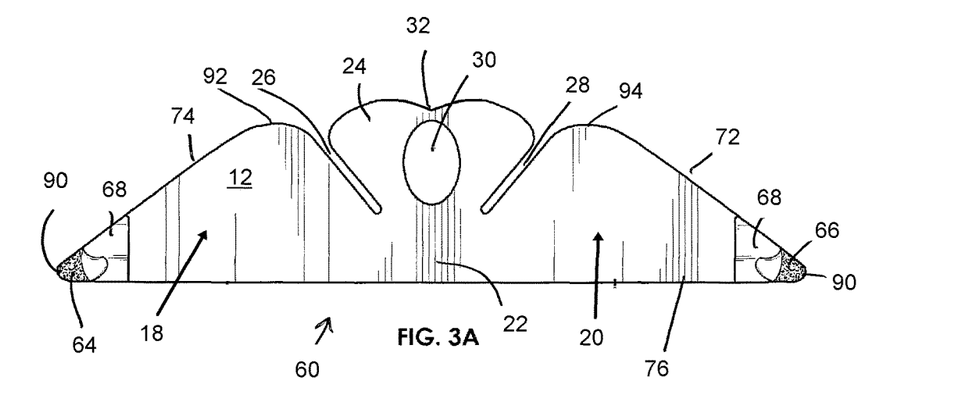
FIG. 3A is a schematic illustration of a fifth embodiment of a bra liner in accordance with the present invention similar to the embodiment shown in FIG. 1A but including adhesive enhancements.
Figure 3B:
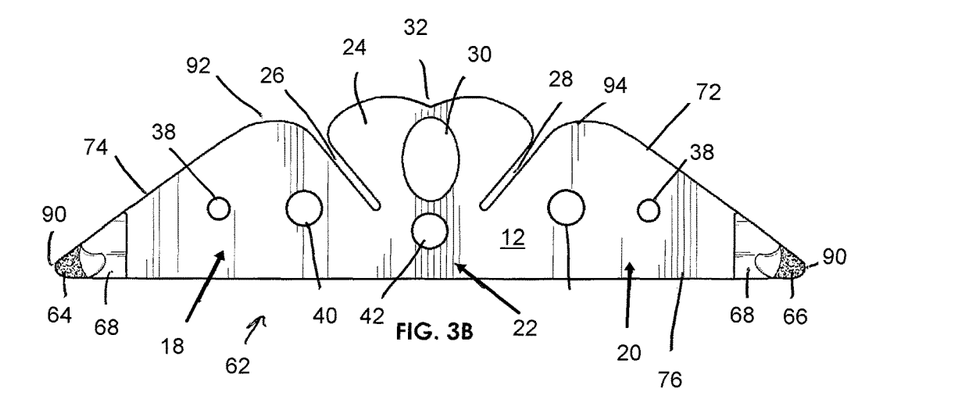
FIG. 3B is a schematic illustration of a sixth embodiment of a bra liner in accordance with the present invention similar to the embodiment shown in FIG. 1B but including adhesive enhancements.

FIGS. 3A and 3B show bra liners 60, 62 similar to bra liners 10, 36, respectively, but include adhesive portions 64, 66. A left adhesive portion 64 is situated on the left wing 18 while a right adhesive portion 66 is situated on the right wing 20. The adhesive portions 64, 66 may be small, generally triangular portions at the extreme left and right edges of the body 16. The size of the adhesive portions 64, 66 may vary as desired and may be dependent, for example, on the size and/or weight of the body 16. The adhesive portions 64, 66 are situated at the left and right tips or tip regions of the body 16.

The type of adhesive applied to the surface 12 of the body 16 to provide the adhesive portions 64, 66 may be any known to those skilled in the art, e.g., an adhesive capable of adhering to material from which a bra is made. Alternative techniques to incorporate adhesive into the body 16 at the tip regions or onto the surface 12 at the tip regions may also be used in the invention.

A cover strip 68 is initially placed over each of the adhesive portions 64, 66, and removed when the adhesive portions 64, 66 are sought to be used to adhere the bra liner 60, 62 to the bra. The adhesive portions 64, 66 may be provided on the any of the bra liners disclosed herein.

Figure 3C:
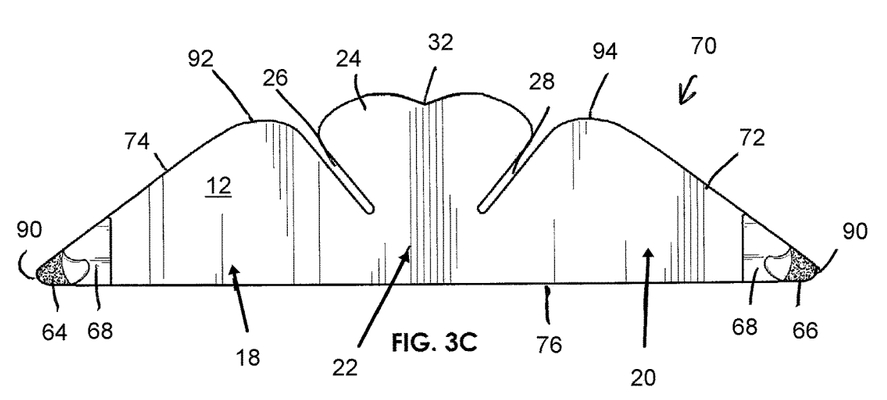
FIG. 3C is a schematic illustration of a seventh embodiment of a bra liner in accordance with the present invention including adhesive enhancements.

FIG. 3C shows a variant of a bra liner 70 which does not include any cut-outs. The body 16 is a solid throughout. Bra liner 70 includes adhesive portions 64, 66. Also, bra liner 70 includes reference numbers representing an upper right peripheral border 72, an upper left peripheral border 74 and a bottom border 76. The slit 26 is a radial cut running downward from the upper left peripheral border 74 toward the centerline C while the slit 28 is a radial cut running downward from the upper right peripheral border 72 toward the centerline C. The slits 26, 28 are centered, defining thereby further the right and left triangular portions.

The material from which the body 16 is made is preferably a material, or more than one material, that is capable of absorbing body perspiration, sweat. At least a portion of this material is preferably exposed to the breast skin and chest skin to enable absorption of perspiration from the breasts skin and chest skin. The exposure may be direct exposure through contact with the breasts and chest or indirect exposure through an air gap between the material and the breasts and chest.

Moreover, the bra liners disclosed herein may be used to embrace individually each person's breasts. The bra liners serve to provide an absorbent material between each breast and the chest area below the breast, as well as separately each breast from the other. In the former case, the left and right wings 18, 20 primarily serve this function while in the latter case, the flap 24 of central portion 22 primarily serves this function. That is, when disposed in place, a bra liner in accordance with the invention provides double sheet protection absorbent inferiorly, separating each breast against the chest and medially against the other person's breast.

Referring now to FIGS. 4A-4G, a method for using the bra liner 10 will be explained, but the same method may be used for the other bra liners disclosed herein. Moreover, the disclosed method does not limit the use of the bra liner and other placement and use methods and techniques may be used without deviating from the scope and spirit of the invention.

Figure 4A:
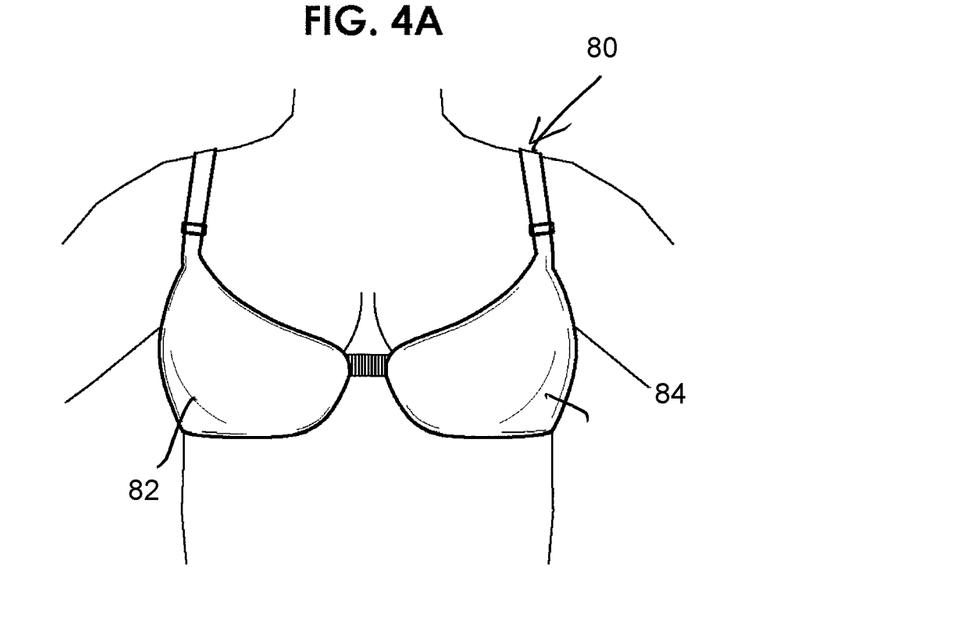
FIGS. 4A, 4B, 4C, 4D, 4E, 4F and 4G are schematic illustrations showing stages in a method for using the bra liner in accordance with the embodiment shown in FIG. 1A of the present invention.
Figure 4B:
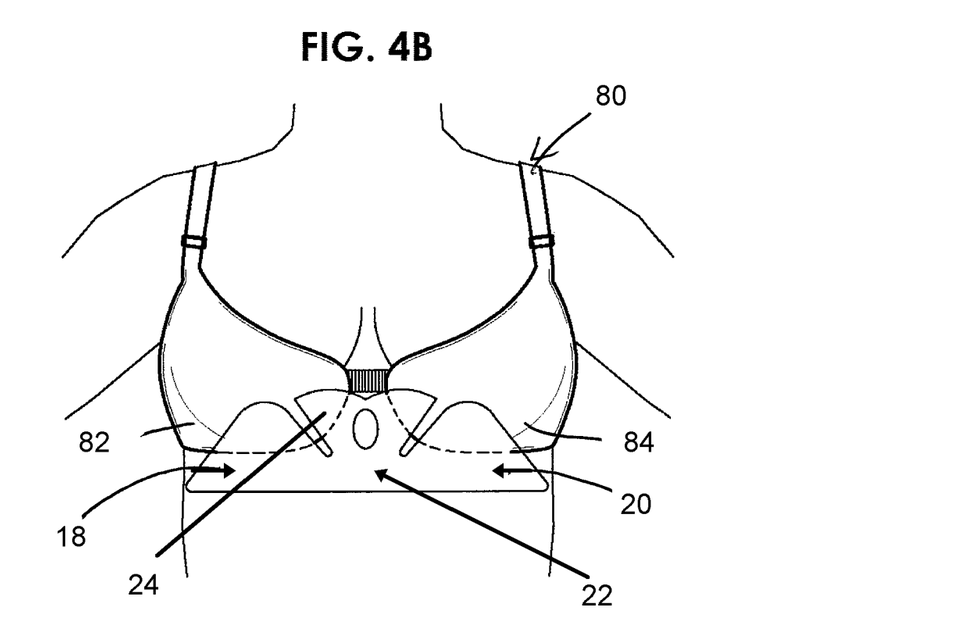
Figure 4C:
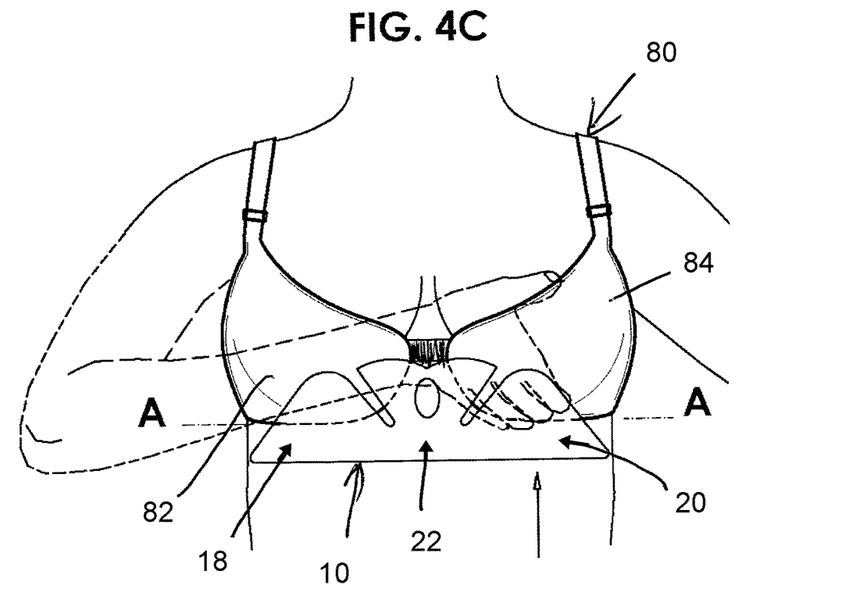
Figure 4D:
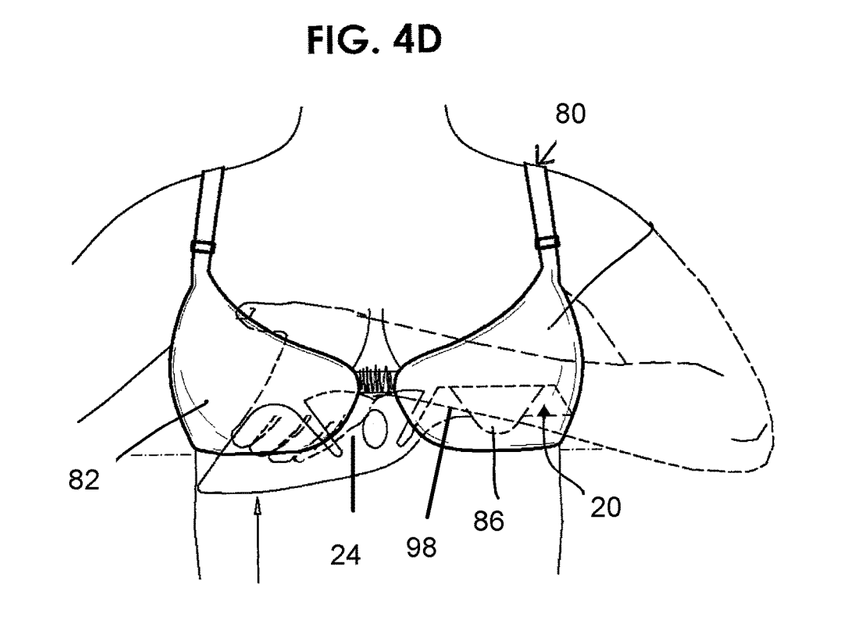

FIG. 4A shows a bra 80 in place on a woman. As a first stage to use the bra liner 10, the bra liner 10 is positioned over the lower edges of the bra 80 with the left and right wings 18, 20 over the left and right bra cups 82, 84, respectively, as shown in FIG. 4B. FIG. 4C shows inward pushing of the right wing 20 of bra liner 10, using fold line A as a fulcrum, with one hand while the second hand may help with lifting up of the bra cup 84, to place the right wing 20 of the bra liner 10 between the breast and the chest. During this placement, the upper triangular foldable part 86 of right wing 20 is folded outward (forward) about the fold line A relative to the non-foldable part 98 of the right wing 20 (see FIG. 4D). FIG. 4D also shows the inward pushing of the left wing 18 of bra liner 10, using line A as a fulcrum, with one hand while the second hand may help with lifting up of the bra cup 82. During this placement, the upper triangular foldable part 88 of the left wing 18 of the bra liner 10 is folded outward (forward) about the fold line A relative to the non-foldable part 96 of the left wing 18 (see FIG. 4E). The central portion 22 and flap 24 are thus positioned under the bra 80 (see FIG. 4E).

Figure 4E:
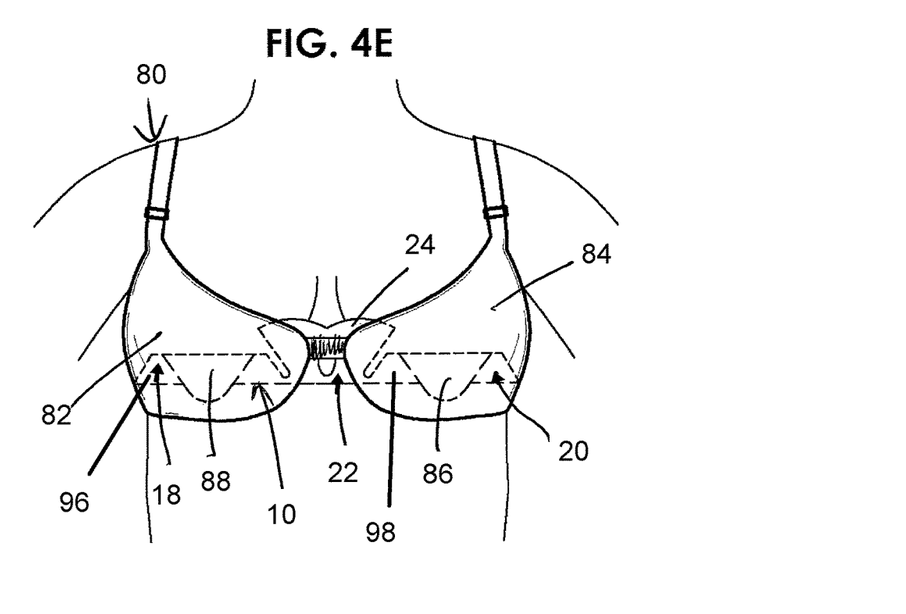
Figure 4F:
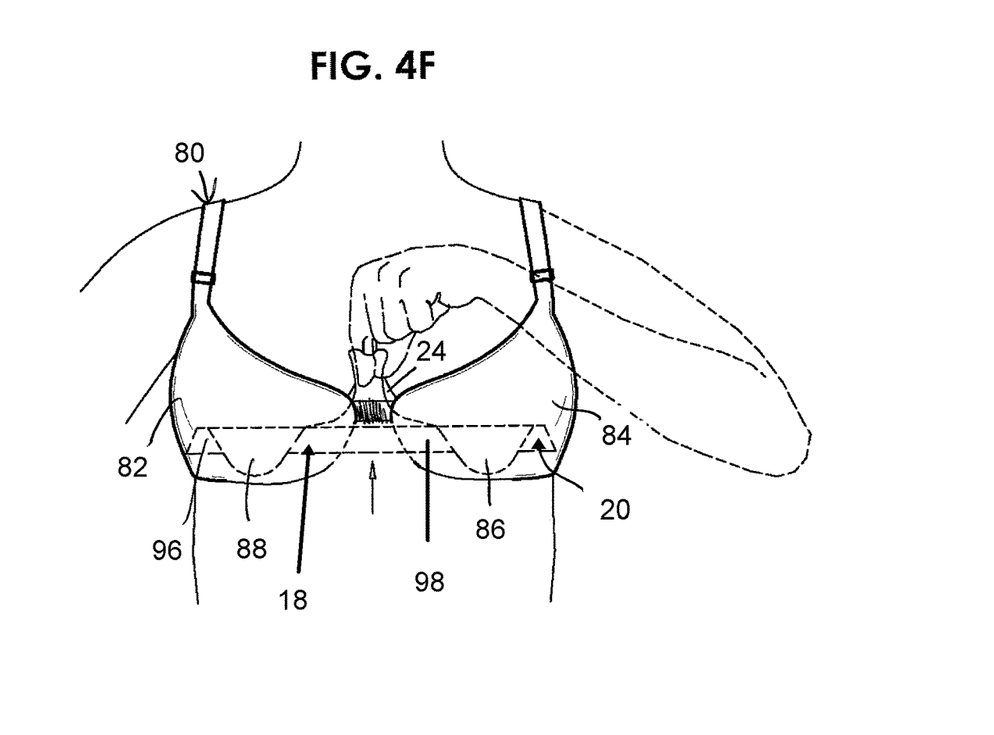
Figure 4G:
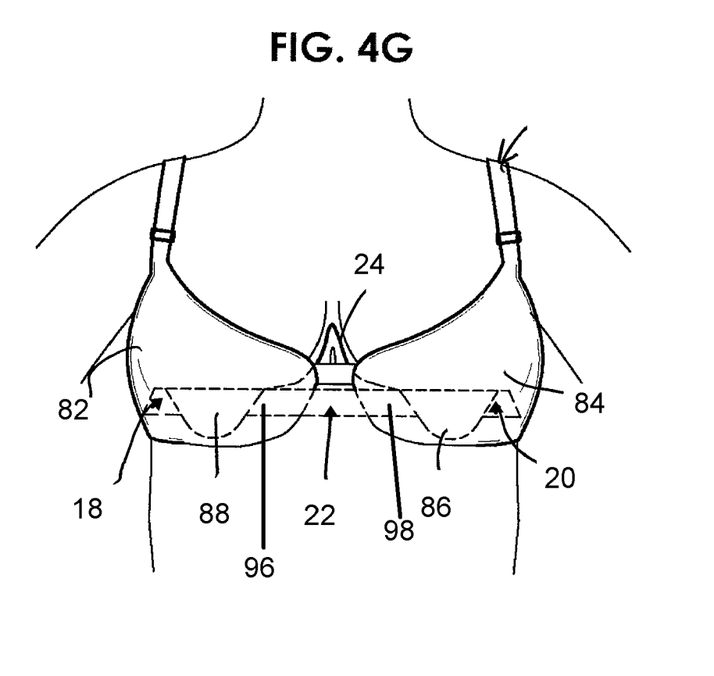

The left and right wings 18, 20 are dimensioned to enable the left upper triangular foldable part 88 and the right upper triangular foldable part 86 to extend, when folded about fold line A, from the fold line A to extend over the non-foldable part 96, 98, of the left and right wings 18, 20, respectively, below the fold line A of the bra liner as shown in FIGS. 4E and 4F. The left and right wings 18, 20 may be dimensioned so that the top of the triangular foldable parts 88, 86, when folded about fold line A, lies on the respective non-foldable parts 96, 98 (not shown) or extends to a location below the bottom 76 of the body 16 (as shown).

This ability to enable the extension of the left upper triangular part 88 and the right upper triangular part 86 is also facilitated by appropriate formation of the slits 26, 28. Thus, from the fold line A, the bra liner 10, when folded, has a double layer of the body 16 formed by a part 96 of the left wing 18 that is not folded and an overlying portion of the upper left triangular part 88. Similarly, from the fold line A, the bra liner has a double layer of the body 16 formed by a part 98 of the right wing 20 that is not folded and an overlying portion of the upper right triangular part 86.

Note that when the left upper triangular part 88 and the right upper triangular part 86 are folded about fold line A, the only portion of the bra liner 10 above fold line A is part of the central portion 22 between the left and right wings 18, 20, and specifically the flap 24 (see FIGS. 4E and 4F).Other than the central portion 22, no other part of the bra liner 10, or any of the other bra liners disclosed herein, remains above the fold line A after the left upper triangular part 88 and the right upper triangular part 86 are folded about fold line A.

Now, to provide the separation between the breasts, the flap 24 is folded about the centerline C to cause one portion on one side of the centerline C to face the left breast and the other portion on the other side of the centerline C to face the right breast, The fold is an outward fold so that the ends of the flap 24 are brought forward away from the chest while the bend at the centerline C is against the person's chest.

The adhesive portions 64, 66 of the bra liner 60, 62, 70, when present, are pressed against an inner surface of the bra 80 after the protective cover strips 68 are removed.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

What is claimed is:

1. A bra liner, comprising:
   a planar body having at least three outer straight sides and including a left portion, a right portion and a central portion between said left and right portions, said central portion including a foldable flap separated from said left and right portions,
   said body comprising absorbent material; and
   wherein said body has a truncated triangular shape having a left corner at a lower left region of said left portion, a right corner at a lower right region of said right portion, and a bottom peripheral edge that is common to said right, left and central portions and forms a lower outer straight side of said body between said left and right corners, an angled left part of said left portion forming a left outer straight side of said body, and an angled right part of said right portion forming a right outer straight side of said body,
   said left corner of said body includes a peripheral edge that directly connects a left end of said lower outer straight side to said left outer straight side,
   said right corner of said body includes a peripheral edge that directly connects a right end of said lower outer straight side to said right outer straight side, said left corner and said right corner being distanced from said central portion such that said lower outer straight side, said left outer straight side and said right outer straight side are between said left corner and said right tip region,
   said left outer straight side extending at an angle upward from said left corner and inward from said left corner toward said central portion,
   said right outer straight side extending at an angle upward from said right corner and inward from said right corner toward said central portion.

2. The bra liner of claim 1, wherein said body has an outer facing surface which is an outermost surface of the bra liner and an inner facing surface which is an innermost surface of the bra liner, and said central portion includes a single hole extending entirely through said body from said outer facing surface to said inner facing surface and which is surrounded by material of said body.

3. The bra liner of claim 1, wherein said body has an outer facing surface which is an outermost surface of the bra liner and an inner facing surface which is an innermost surface of the bra liner, and said right and left portions each include at least one hole extending entirely through said body from said outer facing surface to said inner facing surface and which is surrounded by material of said body.

4. The bra liner of claim 1, wherein said body comprises a three-part absorbent flat sheet.

5. The bra liner of claim 1, wherein said left and right portions each have a generally triangular foldable part and a non-foldable part, said left outer straight side of said left portion being a leftward peripheral edge of both said triangular foldable part and said non-foldable part of said left portion, said right outer straight side of said right portion being a rightward peripheral edge of both said triangular foldable part and said non-foldable part of said right portion.

6. The bra liner of claim 5, wherein said body includes a first elongate slit between said central portion and said triangular foldable part of said left portion and a second elongate slit between said central portion and said triangular foldable part of said right portion, said first and second elongate slits extending downward from an upper edge of said body and inward, said first elongate slit extending from a first curved portion at a top of said left portion, said first curved portion connecting an edge of said left portion defining said first elongate slit and said left outer straight side, said second elongate slit extending from a second curved portion at a top of said right portion, said second curved portion connecting an edge of said right portion defining said second elongate slit and said right outer straight side.

7. The bra liner of claim 6, wherein said left and right portions are foldable about a fold line passing through inward ends of said first and second elongate slits and passing through said left and right outer straight sides.

8. The bra liner of claim 1, wherein said flap includes at least one stitch line enabling removal of a portion of said flap by tearing of said flap along each of said at least one stitch line.

9. The bra liner of claim 1, further comprising:
an adhesive portion at each of said left and right corner; and
a respective cover strip covering each of said adhesive portions, whereby said cover strips are removable to enable adhesive attachment of said body to a bra.

10. The bra liner of claim 1, wherein said left and right portions each have a generally triangular foldable part and a non-foldable part, said body including a first elongate slit between said central portion and said triangular foldable part of said left portion and a second elongate slit between said central portion and said triangular foldable part of said right portion, said first and second elongate slits extending downward from an upper edge of said body and inward, further comprising:
an adhesive portion at each of said left and right corners; and
a respective cover strip covering each of said adhesive portions, whereby said cover strips are removable to enable adhesive attachment of said body to a bra.

11. The bra liner of claim 1, wherein said left portion is part of a left wing and said right portion is part of a right wing, said central portion being connected to said right and left wings, and wherein said left corner includes a first curved portion directly connected at one end to said lower outer straight side and at an opposite end to said left outer straight side and said right corner includes a second curved portion directly connected at one end to said lower outer straight side and at an opposite end to said right outer straight side.

12. The bra liner of claim 1, wherein said body has an outer facing surface and an inner facing surface, said flap including a single hole extending entirely through said body from said outer facing surface to said inner facing surface and which is surrounded by material of said body.

13. A bra liner, comprising:
a planar body including a left portion, a right portion and a central portion between said left and right portions, said central portion including a flap separated from said left and right portions;
said body comprising absorbent material; and
said flap including at least one stitch line enabling removal of a portion of said flap by tearing of said flap along each of said at least one stitch line.

14. The bra liner of claim 13, wherein said left and right portions each have a generally triangular foldable part and a non-foldable part, and said body includes a first elongate slit between said central portion and said triangular foldable part of said left portion and a second elongate slit between said central portion and said triangular foldable part of said right portion, said first and second elongate slits extending downward from an upper edge of said body and inward.

15. The bra liner of claim 14, wherein said body has a truncated triangular shape having a bottom that is common to said right, left and central portions, an angled left side of said left portion forming a left side of the truncated triangular shape of said body and an angled right side of said right portion forming a left side of the truncated triangular shape of said body.

16. The bra liner of claim 13, further comprising:
an adhesive portion at a tip region of each of said right and left portions; and
a respective cover strip covering each of said adhesive portions, whereby said cover strips are removable to enable adhesive attachment of said body to a bra.

\* \* \* \* \*

UNITED STATES PATENT AND TRADEMARK OFFICE
CERTIFICATE OF CORRECTION

PATENT NO. : 10,653,563 B2
APPLICATION NO. : 14/802047
DATED : May 19, 2020
INVENTOR(S) : Donna Lilien

It is certified that error appears in the above-identified patent and that said Letters Patent is hereby corrected as shown below:

In the Claims

Claim 1, Column 8, Line 31, after "right", delete "tip" and insert --corner--; and
Claim 1, Column 8, Line 32, delete "region".

Claim 9, Column 9, Line 20, after "right", delete "corner" and insert --corners--.

Signed and Sealed this
Thirtieth Day of June, 2020

Andrei Iancu
*Director of the United States Patent and Trademark Office*